(12) United States Patent
Hennessy et al.

(10) Patent No.: US 12,343,500 B2
(45) Date of Patent: Jul. 1, 2025

(54) ULTRASONIC INFUSION MONITOR

(71) Applicant: CAREFUSION 303, INC., San Diego, CA (US)

(72) Inventors: Maurice James Hennessy, Limerick (IE); Ronald Hidalgo, Killaloe (IE); Kevin O'Brien, Thurles (IE); Thomas Cleary, Nenagh (IE)

(73) Assignee: CAREFUSION 303, INC., San Diego, CA (US)

( * ) Notice: Subject to any disclaimer, the term of this patent is extended or adjusted under 35 U.S.C. 154(b) by 346 days.

(21) Appl. No.: 17/900,350

(22) Filed: Aug. 31, 2022

(65) Prior Publication Data
US 2023/0061369 A1 Mar. 2, 2023

Related U.S. Application Data

(60) Provisional application No. 63/240,324, filed on Sep. 2, 2021.

(51) Int. Cl.
| | | |
|---|---|---|
| *A61M 5/168* | (2006.01) | |
| *A61M 39/10* | (2006.01) | |
| *G01F 1/66* | (2022.01) | |
| *G01F 1/667* | (2022.01) | |

(52) U.S. Cl.
CPC .... *A61M 5/16886* (2013.01); *A61M 5/16804* (2013.01); *A61M 39/10* (2013.01); *G01F 1/662* (2013.01); *G01F 1/667* (2013.01)

(58) Field of Classification Search
CPC .......... A61M 5/16886; A61M 5/16804; A61M 39/10; G01F 1/662; G01F 1/667
See application file for complete search history.

(56) References Cited

U.S. PATENT DOCUMENTS

| | | | | |
|---|---|---|---|---|
| 3,906,791 | A * | 9/1975 | Lynnworth | G01F 1/66 |
| | | | | 73/861.29 |
| 4,754,650 | A * | 7/1988 | Smalling | G01N 29/024 |
| | | | | 73/861.28 |
| 4,930,358 | A * | 6/1990 | Motegi | G01F 1/662 |
| | | | | 73/861.28 |

(Continued)

FOREIGN PATENT DOCUMENTS

| | | |
|---|---|---|
| WO | WO-2008053193 A1 | 5/2008 |
| WO | WO-2014029404 A1 | 2/2014 |
| WO | WO-2015191775 A1 | 12/2015 |

OTHER PUBLICATIONS

Extended European Search Report for Application No. 22193621.4, dated Jan. 23, 2023, 8 pages.

*Primary Examiner* — Helen C Kwok

(57) ABSTRACT

A system and method for detecting a flow rate using ultrasound is disclosed. A flow rate detector includes a disposable conduit section and a reusable sensor chassis, the chassis configured to fit over an outer surface of the conduit section, the chassis configured to attach along a length of the of the disposable conduit section, and including first and second transducers configured to, when the reusable chassis is attached to the conduit section, measure a flow rate of a fluid passing through the conduit section by measuring an ultrasonic transmission between the first and second transducers through the fluid. The ultrasonic transmission is reflected at least once off of the inner surface of the disposable conduit before being received at the second transducer.

18 Claims, 8 Drawing Sheets

(56) References Cited

U.S. PATENT DOCUMENTS

| | | | | |
|---|---|---|---|---|
| 5,001,936 A * | 3/1991 | Baumoel | ............... | G01F 1/662 |
| | | | | 73/861.28 |
| 5,090,252 A * | 2/1992 | Tschirner | ............... | G01F 1/66 |
| | | | | 73/861.28 |
| 5,372,047 A * | 12/1994 | Russwurm | ............ | G01F 1/662 |
| | | | | 73/861.27 |
| 5,440,936 A | 8/1995 | Spani et al. | | |
| 5,463,906 A | 11/1995 | Spani et al. | | |
| 2004/0123666 A1 * | 7/2004 | Ao | ............... | G10K 11/165 |
| | | | | 73/644 |
| 2011/0271769 A1 * | 11/2011 | Kippersund | ............ | G01F 1/86 |
| | | | | 73/861.28 |
| 2012/0272749 A1 * | 11/2012 | Lang | ............... | G01F 1/662 |
| | | | | 73/861.25 |
| 2012/0285260 A1 * | 11/2012 | Mueller | ............... | G01F 1/667 |
| | | | | 73/861.27 |
| 2014/0081165 A1 * | 3/2014 | von Bahr | ............ | A61B 5/097 |
| | | | | 600/532 |
| 2014/0114238 A1 * | 4/2014 | Lee | ............... | A61M 5/16831 |
| | | | | 604/67 |
| 2017/0102254 A1 * | 4/2017 | Drachmann | ............ | G01F 1/662 |
| 2017/0160240 A1 * | 6/2017 | Fan | ............... | G01F 15/18 |
| 2018/0160948 A1 * | 6/2018 | Takagi | ............... | A61B 5/1455 |
| 2019/0265203 A1 * | 8/2019 | Leaders | ............ | G01N 29/222 |
| 2019/0285450 A1 * | 9/2019 | Tsukigi | ............... | G01F 1/667 |
| 2022/0373372 A1 * | 11/2022 | Kishore | ............... | G01F 1/74 |

\* cited by examiner

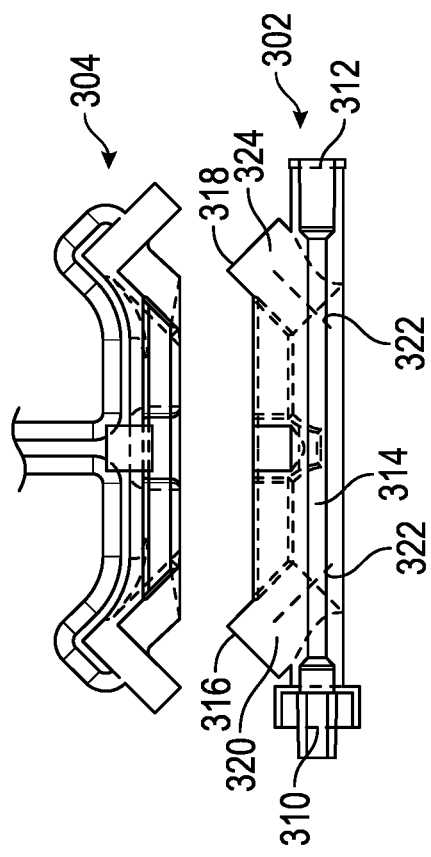
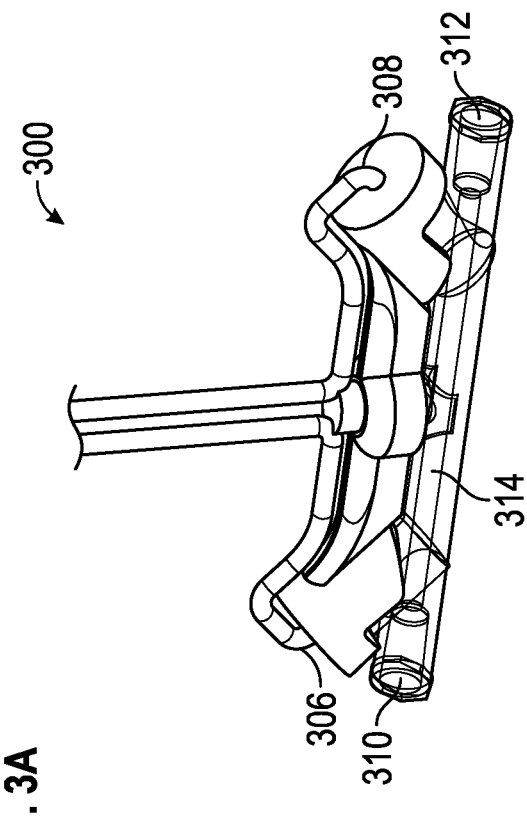
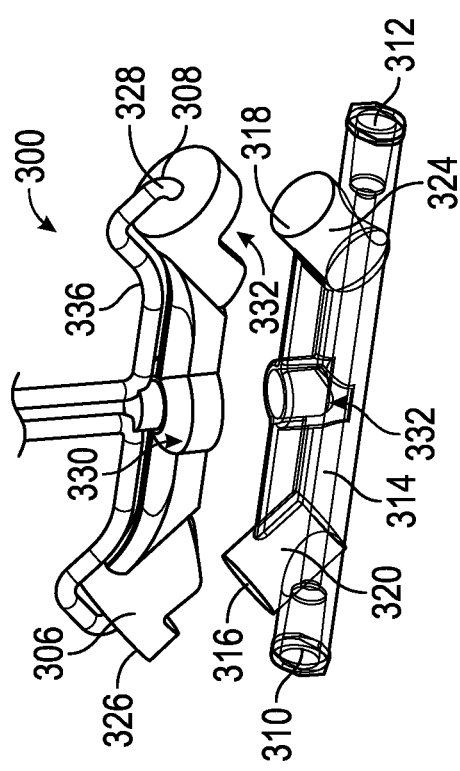
FIG. 3A
FIG. 3B
FIG. 3C

ULTRASONIC INFUSION MONITOR

CROSS REFERENCE TO RELATED APPLICATIONS

This application claims priority to U.S. Provisional Patent Application No. 63/240,324, entitled ULTRASONIC INFUSION MONITOR, filed on Sep. 2, 2021, the disclosure of which is incorporated herein by reference in its entirety.

TECHNICAL FIELD

This application relates generally to determining flow parameters of a fluid in an intravenous (IV) administration line.

BACKGROUND

Infusion devices such as pumps can, in certain circumstances, introduce air into the fluid line ("air-in-line") or misestimate the quantity of fluid delivered ("over-infusion" or "under-infusion"). Clinicians may experience under-infusions at high flow rates as well as critical pump failures, many of which may not be noticed until after the fact. These scenarios, whether actual failures or based on faulty estimates, can impact the infusion device, the resources it uses (e.g., power, alerting, processor cycles, etc.) and may affect the care provided via the infusion device.

Infusion devices flow rate detection accuracy can range from ±2% all the way to ±10% under nominal conditions. However, this accuracy range may not account for the wide range of user interactions and environmental changes that pumps are subjected to. Also, air-in-line (AIL) can be a potential risk to patients when fluids or medications are delivered into the body through a blood vessel. If a significant amount of air is introduced into a blood vessel, it can travel through the blood vessels and become lodged in critical organs such as the brain, heart, or lungs.

Flow rate inaccuracies and air-in-line manifestations can result from, but are not limited to various factors: Pump variations, for example, tolerances and differences in pump calibration, or wear of components. Environmental characteristics, for example, temperature or humidity, which may vary significantly between home care and hospital environments. Head height of LVPs (the head of pressure feeding the system). Dimensional variations in medications and disposables such as syringes or IV sets, for example in viscosities and physical characteristics. And, user error, for example, a clinician unintentionally misloading an infusion set or twisting IV tubing.

Additionally, notification of infusion device issues typically occurs via means of customer complaints. This is too late, as at this point a critical issue may have already occurred, potentially reducing the availability of infusion device(s) or quality of care.

SUMMARY

The subject technology utilizes ultrasonic transit time to monitor flow rate accuracy in an intravenous (IV) administration line. According to various aspects, a transit-time flow measurement system includes two ultrasonic transducers that function as both ultrasonic transmitter and receiver. In this regards, a flow meter operates by alternately transmitting and receiving a burst of sound energy between the two transducers and measuring the transit time that it takes for sound to travel between the two transducers. The difference in the transit time measured is directly and exactly related to the velocity of the liquid in the IV line. One advantage includes improving the accuracy of an infusion pumps flow rate measurements and air-in-line detection through a feedback detection loop.

According to various aspects disclosed herein, a flow rate detector comprising a reusable sensor chassis configured to fit over an outer surface of a disposable conduit section, the reusable sensor chassis configured to attach along a length of the of the disposable conduit section, and comprising first and second transducers configured to, when the reusable chassis is attached to a disposable conduit section, measure a flow rate of a fluid passing through the conduit section by measuring an electronic transmission between the first and second transducers through the fluid. The electronic transmission is reflected at least once off of an inner surface of the disposable conduit section between the first and second transducers. Other aspects include corresponding systems, methods, and computer program products for implementation of the disclosed flow rate detector.

According to various aspects disclosed herein, a flow rate detector system comprises: a disposable conduit section comprising: (1) an input connector and an output connector configured to connect to an IV tubing, (2) a fluidic channel enabling fluid to flow between the input and output connectors, and (3) first and second transducer guides formed with an outer surface of the disposable conduit, each transducer guide configured to position a respective transducer for transmission to or from each respective transducer to occur at an angle offset from the fluidic channel, and such that a transmission from one of the respective transducers passes through a first portion of the fluidic channel, reflects at least once off of an inner surface of the fluidic channel, and passes through a second portion of the fluidic channel be received at the other respective transducer.

In some implementations, the system comprises a reusable transducer chassis configured to fit over and attach along a length of the disposable conduit section, the reusable transducer chassis comprising first and second transducers positioned such that, when the reusable transducer chassis is fitted over and attached to the disposable conduit section, the first transducer is aligned with the first transducer guide of the disposable conduit section and the second transducer is aligned with the second transducer guide to enable a transmission from the first transducer to pass through the first and second portions of the fluidic channel. In some implementations, the reusable transducer chassis comprises a first inverted cavity housing the first transducer and a second inverted cavity housing the second transducer, each inverted cavity configured to slide over a corresponding transducer guide and align a corresponding transducer with the corresponding transducer guide when the reusable transducer chassis is attached along the length of the disposable conduit. In some implementations, the at least a portion of each transducer guide is cylindrical with a flat surface configured to slide into a respective inverted cavity of the reusable transducer chassis and interface with a floor of the respective inverted cavity when the reusable transducer chassis is attached along the length of the disposable conduit. Other aspects include corresponding apparatuses, methods and computer program products for implementation of the disclosed system.

According to various aspects disclosed herein, a method comprises providing a disposable conduit for sensing a flow rate and comprising first and second transducer guides formed with an outer surface of the disposable conduit, each transducer guide configured to position a respective transducer of a sensor chassis such that a transmission to or from each respective transducer occurs at an angle offset from a fluidic channel within the disposable conduit, and such that a transmission from one of the respective transducers passes through a first portion of the fluidic channel, reflects at least once off of an inner surface of the fluidic channel, and passes through a second portion of the fluidic channel to be received at the other respective transducer. The method may further comprise connecting the disposable conduit to a reusable transducer chassis configured to fit over and attach along a length of the disposable conduit, the reusable transducer chassis comprising first and second transducers positioned such that, when the reusable transducer chassis is fitted over and attached to the disposable conduit, the first transducer is aligned with the first transducer guide of the disposable conduit and the second transducer is aligned with the second transducer guide to enable a transmission from the first transducer to pass through the first and second portions of the fluidic channel.

According to various aspects, the method may further comprise connecting the disposable conduit to an intravenous (IV) tubing; transmitting, using the first transducer, an ultrasonic wave through a portion of the disposable conduct corresponding to the first transducer guide, and through a fluid within the disposable conduit, in a manner that the ultrasonic wave is reflected off of an inner surface of the disposable conduit before being received at the second transducer, through the second transducer guide; measuring the ultrasonic wave using the second transducer to obtain a measured value; and determining a flow rate of the fluid based on the measured value. The ultrasonic wave may be reflected two or more times off of the inner surface of the disposable conduit before being received at the second transducer. Other aspects include corresponding systems, apparatuses, and computer program products for implementation of the disclosed method.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

FIGS. 3A, 3B, 3C, 3D, and 3E depict various examples of a ultrasonic flow rate detector for measuring downstream flow rate of an infusion device, according to various aspects of the subject technology.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

In a typical infusion operation, an end-user such as a clinician will select a flow rate and a VTBI (volume to be infused). The flow rate is typically in ml/hr and the VTBI is typically in ml. By using these two known inputs, the pump then calculates the total duration that it must operate to complete the infusion:

$$\text{Duration} = \frac{VTBI}{\text{Flow Rate}} \qquad (\text{Eq. 1})$$

To calculate if the required Duration of the first equation is already met, the pump may obtain feedback from an encoder wheel which is attached to the pumping motor. The number of encoder-per-revolution of the encoder wheel is known. A motor speed will also be pre-determined at a given flow rate. Therefore, if the pump completes a number of encoders at the pre-determined motor speed, it estimates that the Duration is already completed. And by virtue of Eq. 1, the VTBI is complete:

Number of Encoders=(Motor Speed)×(Encoder per revolution)×(Duration)  (Eq. 2)

The estimation of the volume infused as described above is a simplified explanation. The pre-determined Motor Speed maybe identified by calibration at relevant points along the Flow Rate range as defined by the manufacturer. A correction coefficient in the calculation may also be introduced to compensate for factors that may contribute to deviate from the calculation described above. Nevertheless, the pump's source of feedback may only be from the motor encoder and has the potential to assume that the VTBI is completed.

Figure 1B:
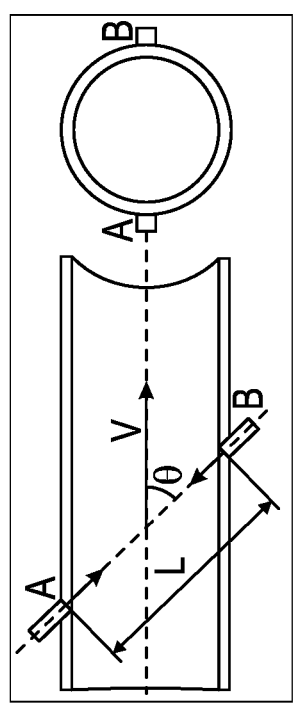
FIGS. 1A and 1B depict first example methods for measuring downstream flow rate of an infusion device by detection of ultrasonic transit time, according to various aspects of the subject technology.
Figure 1A:
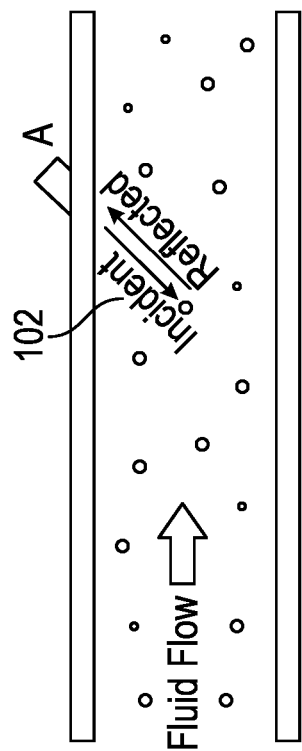

FIGS. 1A and 1B depict first example methods for measuring downstream flow rate of an infusion device by detection of ultrasonic transit time, according to various aspects of the subject technology. A transit-time flow measurement system may utilize two or more ultrasonic transducers that function as both ultrasonic transmitter and receiver. The flow meter of the subject technology may operate by alternately transmitting and receiving a burst of sound energy between the two transducers and measuring the transit time that it takes for sound to travel between the two transducers, through the particular fluid within an tube. The difference in the transit time measured is directly and exactly related to the velocity of the fluid in the tubing.

Figures 3D, 3E:
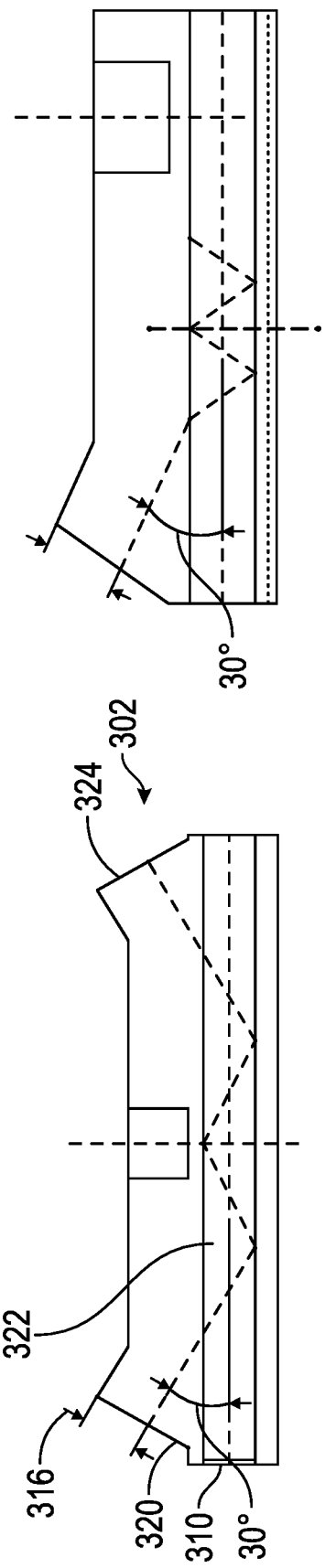

In FIG. 1A, a fluid is moving within the tubing according to a velocity V. Transducers A and B are positioned at opposing sides of the tubing and offset from the tubing by an angle ⊖, and spaced apart by a distance L. In this regard, Tdown is the transit-time of a sound pulse traveling from the upstream transducer A to the downstream transducer B, and Tup is the transit-time from the opposite direction, B to A. In other words:

$$T\text{down}=(D/\sin q)/(c+V^*\cos q), \quad (Eq. 3)$$

$$T\text{up}=(D/\sin q)/(c-V^*\cos q), \quad (Eq. 4)$$

where:
c=speed of sound in the liquid,
D=pipe diameter
V=flow velocity averaged over the sound path.
Solving equations 3 and 4 leads to:

$$V=(D/\sin 2q)^*\Delta T/(T\text{up}^*T\text{down}) \quad (Eq. 5)$$

where:
ΔT=Tdown−Tup
Tdown=Transit time of waves from upstream transmitter to downstream receiver
Tup=Transit time of waves from downstream transmitter to upstream transmitter Parameter q may be dependent on the refractive index of the material, and can be determined using Snell's Law. In the depicted examples of FIGS. 3D and 3E, the refractive angle is set at 30°. The spacing between the two sensors (e.g., flight time) may also be dependent on the velocity of sound for the given medium (e.g., ~1500 m/s for water).

FIG. 1B depicts a modified implementation in which a doppler effect is utilized to measure flow. In the depicted example, reflected ultrasonic sound 102 also measures the fluid velocity by way of incident reflections from the fluid itself rather than an additional transducer B. A relative motion is determined by measuring the frequency shift between the ultrasonic frequency source, the receiver, and the fluid carrier. As there is no particulate typically present in infusate, the subject technology induces a turbulent flow into the measurement zone through a geometry change and then measures the magnitude of this turbulence. The magnitude of this turbulence is then recorded as being proportional to the flow rate.

According to various implementations described herein, pulse-echo air in line monitoring may be used in addition to or in place of ultrasound. In such implementations, sound waves are transmitted to the fluid, reflected and received by the same transmitter that sent it. In both methods, bubbles will influence the velocity, attenuation and the scattering of the sound, thus providing for accurate detection and measurement. The foregoing equations may be adapted to include a variable corresponding to characteristic and/or an expected response (or attenuation) of the fluid medium through which the transmission occurs.

Figure 2B:
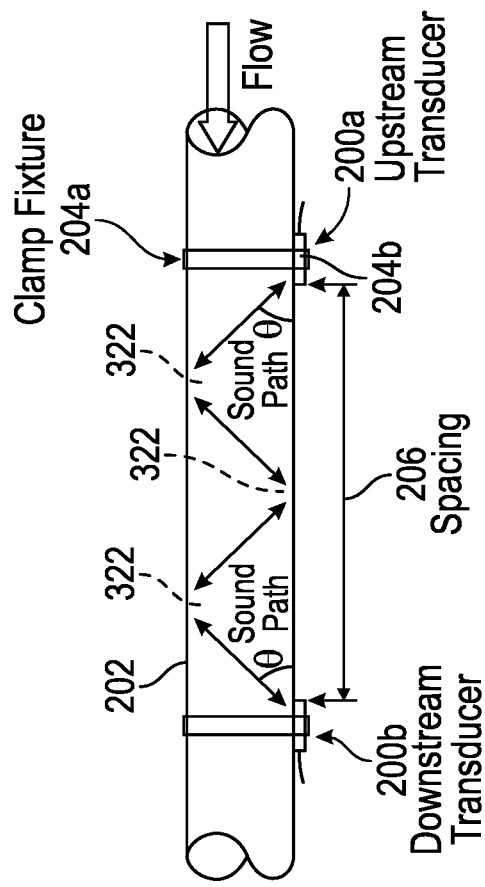
FIGS. 2A and 2B depict second example methods for measuring downstream flow rate of an infusion device by detection of ultrasonic transit time, according to various aspects of the subject technology.
Figure 2A:
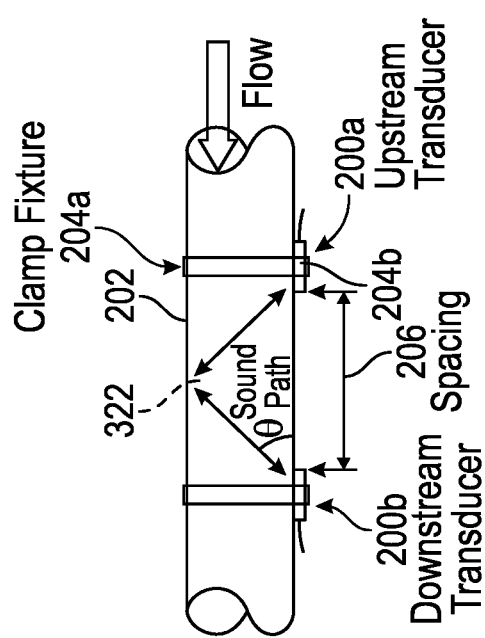

FIGS. 2A and 2B depict second example methods for measuring downstream flow rate of an infusion device by detection of ultrasonic transit time, according to various aspects of the subject technology. According to various implementations, transducers can be mounted in one of three ways: Z-method, V-method and W-method. FIG. 2A depicts the V-method and FIG. 2B depicts the W-method.

In the V-method of FIG. 2A, two transducers, an upstream transducer 200a and a downstream transducer 200b, are mounted on the same side of a fluid conduit 202 (such as an IV tubing). The upstream transducer 200a is positioned closer to the pump and farther away from the infusion site location (e.g., at the patient) than the downstream transducer 200b. The transducers may be mounted by way of respective clamp fixtures 204a and 204b which wrap around the conduit and secure the transducers. Transducers 200a and 200b are offset from the conduit 202 by an angle ⊖, and spaced apart by a spacing 206. The spacing 206 between transducers 200a and 200b is proportional to the angle ⊖. According to various implementations, Conduit 202 is made of a material suitable for consistent reflection of the ultrasound energy. In the depicted examples, angle ⊖ is equal for both transducers, with reflection point 208 being half way between the transducers. When a transmitting transducer transmits its burst of energy, the sound pulse crosses the pipe flow twice before being received by the transducer acting as the receiver, reflecting off of the inner portion of conduit 202 at reflection point 208.

In the W-method of FIG. 2B, the two transducers 200a and 200b are also mounted on the same side of fluid conduit 202. However, the spacing between the two transducers is doubled comparing with V-method. The sound pulse is bounced twice from the other side of the pipe; thus it intercepts the flow four times. This implementation is suitable for smaller conduit sizes such as in common IV tubing sets.

In the Z-method, the two transducers are mounted on opposite sides of the pipe (similar to FIG. 1A) and the sound pulse crosses the pipe flow once. This implementation may be suitable for conduit sizes larger than common IV tubing sets.

The flow rate may be calculated based on the number of interactions with the cylindrical wall, which is further based on incident angle q (which may be equal to the reflection angle). The transit time of each traversal may be the same, which may be further based on the medium through which the wave is traveling. In a V method, for example, the estimated transit time from transducer A to transducer B may be the calculated traverse time X2+the transit time through the acoustic target zone+transducer chassis. In W the estimated transit time may be X4+the transit time through the acoustic target zone+transducer chassis.

For each of the V-method, W-method or Z-method, test flow rates may be implemented for each type of fluid (e.g., each type of medication) and, in some implementations, the size of tubing or conduit (which, e.g., may determine transit time), and respective values measured. The flow rates may then be indexed in a lookup table by the measured values and made available for use by an infusion device (e.g., device 500). For example, the table may be stored in a database (within a non-transitory memory) within the infusion device or made available to the infusion device by a server. Additionally or in the alternative, bias values that correct for a flow rate measured by the infusion device administering a medication (e.g., device 500) may be stored. In this regard, a bias value may be used by the infusion device to correct for a flow rate measured by the infusion device by some other mechanism.

FIGS. 3A, 3B, and 3C depict an example ultrasonic flow rate detector 300 for measuring downstream flow rate of an infusion device, according to various aspects of the subject technology. In the depicted example, flow rate detector 300 employs a custom luer connector/adaptor to facilitate measurements. In this regard, a flow rate detector 300 is designed to be fitted in-line downstream from an infusion device, or connected directly to a luer lock syringe.

Flow rate detector 300 includes a disposable molded conduit 302 and a sensor chassis 304 (e.g., containing one or more transducers) configured to attach to an outer surface of the conduit 302. Conduit 302 and senor chassis 304 are molded, as further described below, to position transducers 200a and 200b at an angle suitable for ultrasonic transmission according to the Z-method, V-method or W-method described with regard to FIG. 2A and FIG. 2B. While the depicted examples of FIGS. 3A, 3B, and 3C are configured for ultrasonic transmission according to the W-method, the flow rate detector 300 may be modified according to the any other method described herein (e.g., by varying the length of the conduit 302). For example, the intravenous set may include an identifier that indicates the type of ultrasonic transmission are supported by the physical design of the set. In some implementations, the identifier may be automatically detected by the infusion device upon loading. In some implementations, the identifier may be provided to the infusion device such as via a barcode scan, wireless tag scan, or through user input via a graphical user interface. Upon detecting the identifier for the set, the flow rate detector 300 or other device connected therewith can adjust the detection method to correspond with the set capabilities.

According to various implementations, flow rate detector 300 includes a disposable conduit section 302 (e.g. a connector/adaptor) and a reusable (e.g., non-disposable) chassis 304. The sensor chassis 304 may form a reusable housing to surround elements of the flow rate detector 300. In some implementations, the sensor chassis 304 may include or form an ultrasonic head piece. In the depicted examples, chassis 304 includes a first transducer 306 and a second transducer 308. Transducers 306, 308 are configured to, when the reusable chassis 304 is attached to the disposable conduit section 302, measure a flow rate of a fluid passing through the conduit section by measuring an electronic transmission transmitted between the first and second transducers through the fluid passing with conduit section 302, as described previously with regard to FIGS. 1A and 1B.

The disposable conduit section 302 includes an input connector 310 and an output connector 312 configured to connect to an IV tubing and/or a medical instrument such as a syringe. Conduit section 302 includes a fluidic channel 314 enabling fluid to flow between the input and output connectors. As depicted, the fluidic channel 314 may be centered along a length of conduit section 302. Conduit section 302 further includes first and second transducer guides 316, 318. According to some implementations, the transducer guides 316, 318 may be formed with an outer surface of the disposable conduit 312 (e.g., from the same material and/or mold). As depicted, a connector 310 may be configured to connect directly to a pump fitting, such as the end of a syringe pump. Each transducer guide 316, 318 is configured to position a respective transducer 306, 308 of chassis 304 such that a transmission to or from each respective transducer occurs at an angle ⊖ offset from the fluidic channel 314 (e.g., from an axis of the channel), and such that a transmission from one of the respective transducers passes through a first portion 320 of the fluidic channel, through the fluid, reflects at least once off of an inner surface 322 of the fluidic channel, and passes through a second portion 324 of the fluidic channel (in some implementations, through the fluid again) to be received at the other respective transducer 306, 308.

The reusable chassis 304 (or ultrasonic head) may be attached to the disposable section 302 to enable measurement. According to various implementations, the reusable transducer chassis 304 is configured to fit over and attach along the length of the disposable conduit section 302. The reusable transducer chassis includes the first and second transducers 306, 308 positioned such that, when the reusable transducer chassis 304 is fitted over and attached to the disposable conduit section 302, the first transducer 306 is aligned with the first transducer guide 316 of the disposable conduit section 302 and the second transducer 308 is aligned with the second transducer guide 318 to enable a transmission from the first transducer 306 to pass through the first and second portions 320, 324 of the fluidic channel.

In some implementations, the reusable transducer chassis 304 includes a first inverted cavity 326 housing the first transducer and a second inverted cavity 328 housing the second transducer. As depicted in FIGS. 3A and 3B, the inverted cavity 328 is configured to slide over a corresponding transducer guide 316, 318 and align a corresponding transducer 306, 308 with the corresponding transducer guide when the reusable transducer chassis 304 is attached along the length of the disposable conduit 302.

As depicted in FIG. 3B, at least a portion of each transducer guide 316, 318 may be cylindrical with a flat surface and configured to slide into a respective inverted cavity 326, 328 of the reusable transducer chassis 304 and interface with a floor 332 of the respective inverted cavity 326, 328 when the reusable transducer chassis 304 is attached along the length of the disposable conduit 302.

In some implementations, the chassis 304 includes an attachment guide at location corresponding to, when the chassis 304 is fitted over and attached to the disposable conduit 302, a corresponding attachment guide 332 on the disposable conduit 302, such that the chassis 304 and the disposable conduit 302 are caused to connect together and align. In some implementations, the reusable transducer chassis 304 and the disposable conduit 302 each comprise a magnet or other ferromagnetic material, respectively, at corresponding locations such that the chassis 304 and the disposable conduit 302 are caused to connect together by a magnetic force and to align each of the first and second transducers with the corresponding transducer guide. The magnetic connection facilitates repeatable measurements by attaching chassis 304 (e.g., the ultrasonic head) to precise target zones.

According to various implementations, the transducers 306, 308 are ultrasound transducers, and the transmission is an ultrasonic wave. Portions of the inner surface of the fluidic channel off of which the transmission reflects are made from or include an ultrasonic reflective material 334 that is different than an ultrasonic transparent material forming other portions of the fluidic channel including portions 336 of the fluidic channel through which the transmission from the transducers 306, 308 pass. The transducers 306, 308 may be electrically connected to an infusion device or monitoring system by way of one or more electrical leads 336. The connection with the infusion device or monitoring system may be used to collect and transfer data using the transducers 306, 308. The connection with the infusion device or monitoring system may be to draw power from the infusion device or monitoring system. For example, some pumps include a powered universal serial bus port that can be used to connect, via a wired interface, with the flow rate detector 300. In such implementations, the infusion device or monitoring system may control the detection and analysis of detected values. In some implementations, the flow rate detector 300 may include a microprocessor or other controller that draws power from the infusion device or monitoring system. The controller may be programmed to perform one or more of the ultrasonic detection features described and generate an output for transmission to the infusion device or monitoring system including collecting measurements from the transducers 306, 308 and/or analyzing the measurements received from the transducers 306, 3098. In the depicted example, the leads 336 are attached to an outer portion of each inverted cavity 326, 328 and electrically and fluidically shielded. As depicted, the shielding of the leads may be ridged and configured to be used as a placement tool. For example, the user may grab the lead portions 336 of the chassis 304 to maneuver the chassis 304 for attachment to the conduit 302.

Figure 4:
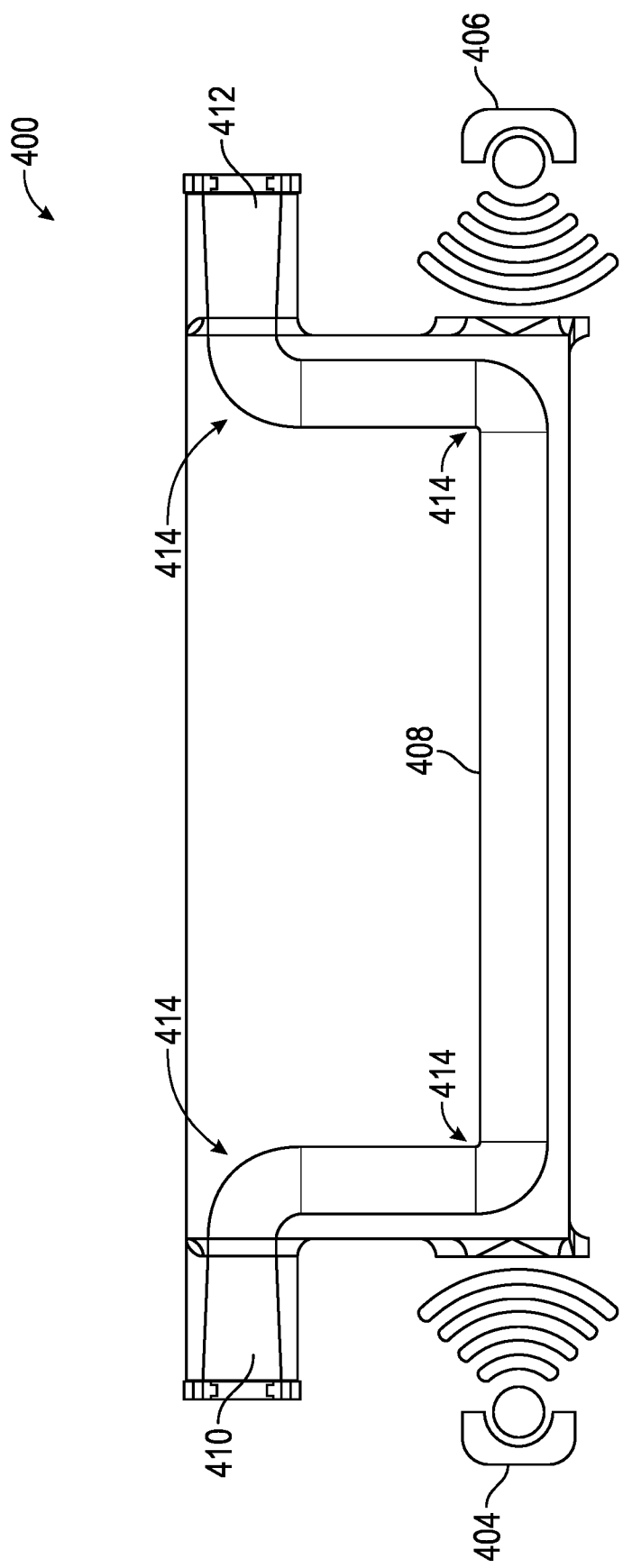
FIG. 4 depicts a second example ultrasonic flow rate detector for measuring a flow rate of an infusion device, according to various aspects of the subject technology.

FIG. 4 depicts a second example ultrasonic flow rate detector 400 for measuring a flow rate of an infusion device, according to various aspects of the subject technology. Similar to other implementations, flow rate detector 400 includes a disposable conduit section 402 and a reusable portion (not shown) that includes transducers 404, 406 (e.g. ultrasonic transducers). In the depicted example, however, transducers 404, 406 are mounted inline with the flow direction 408. In this regard, an elongated conduit section 408 is offset from input and output connectors 410, 412. To avoid interference of the connectors with the transducers, conduit section (e.g. adapter/connector) includes curved portions 414, 416 that curve away from input and output connectors 410, 412, respectively, to place elongated conduit section 408 parallel to an axis 418 of the IV line connected to input and output connectors 410, 412.

Because there are no ultrasonic reflection, signal loss caused by ultrasonic reflections are minimized or eliminated, resulting in an improved accuracy of the transmission and/or measurements.

Figure 5:
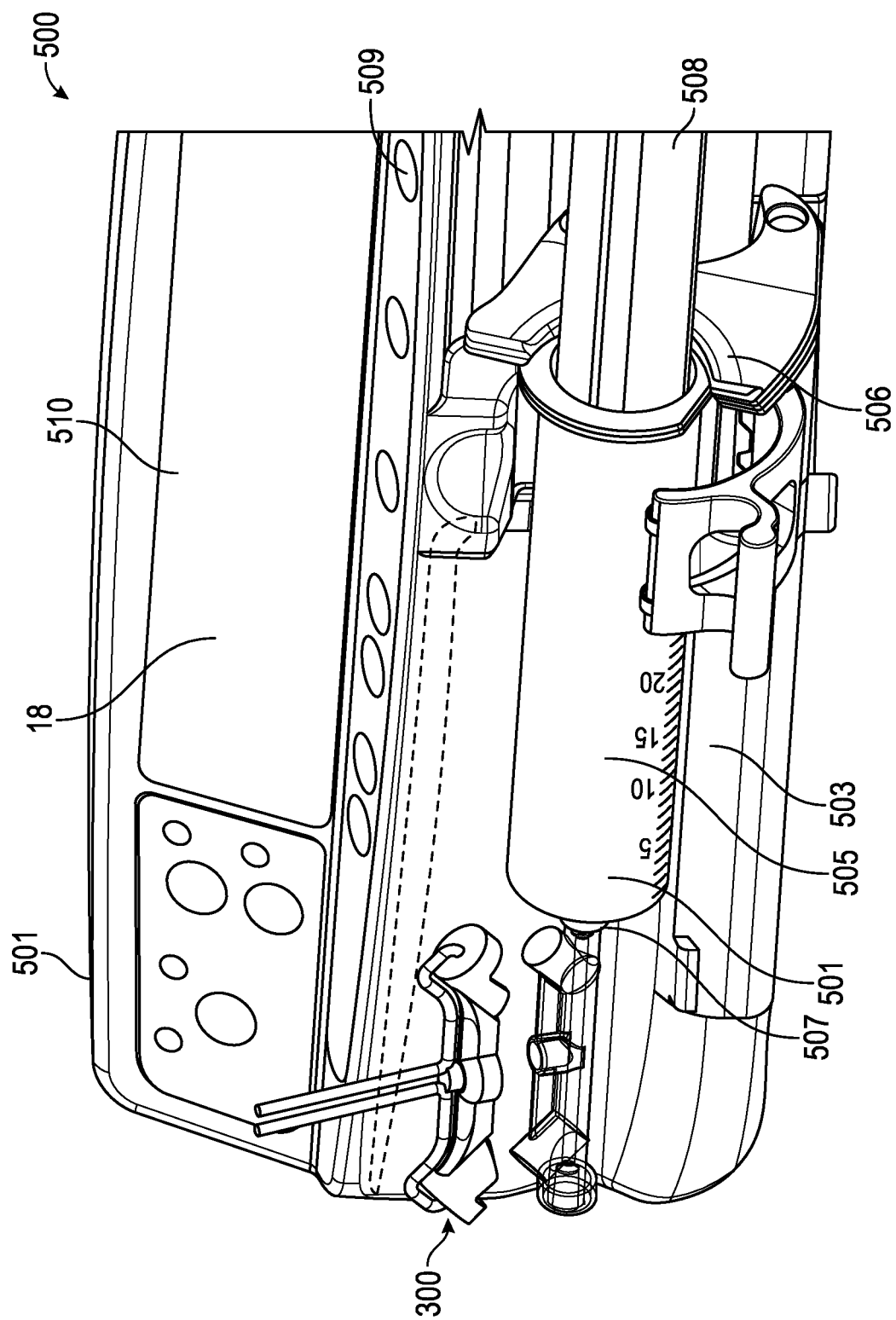
FIG. 5 depicts an example of the disclosed ultrasonic flow rate detector connected to a syringe of an infusion device, according to various aspects of the subject technology.

FIG. 5 depicts an example of the disclosed ultrasonic flow rate detector 300, 400 connected to a syringe of an infusion device 500, according to various aspects of the subject technology. While the depicted infusion device 500 includes a syringe pump with a syringe 501 functioning as a delivery component, other types of infusion devices are also contemplated. For example, infusion device 1 may includes a peristaltic pump that drives a fluid through an intravenous (IV) tube.

Infusion device 500 includes a chassis 502 having a syringe cradle 503 therein which is of appropriate size for receiving of the syringe 501, in particular the syringe barrel 505 thereof.

In the example shown, there is a clip 506 provided to support the syringe barrel 505 in the syringe cradle 503. The syringe pump 500 may be in a state either before or during infusion where the syringe plunger (not shown) is extended out into the syringe barrel 505. The syringe plunger terminates with a syringe piston at one end, which forces fluid from the syringe 501 by way of a force applied at an opposing end, by a driving mechanism acting on the syringe plunger stem 508. The syringe stem 508 is pushed via the driving mechanism when in use, which forces the syringe piston (not shown) through the syringe barrel 505 thereby forcing liquid through the end of the syringe 501.

A user may activate and program the syringe pump 500, via a display 510. The display screen 510 may be a simple LCD (liquid crystal display). The display may be monochromatic, for example, it might only display red, green or grey/black characters. Alternatively, the display 510 might be a more complicated liquid crystal display capable of displaying complex graphics or more complicated characters. The LCD may be backlit, for example, using light emitting diodes (LEDs). In some implementations, the infusion device may include a TFT LCD. A TFT is a thin-film transistor-based LCD technology. In some implementations, the display screen 501 is also a touchscreen such as a capacitive touchscreen.

When programming an infusion device, the user may input parameters by way of an input device 509 such as a keyboard or touchscreen. Input parameters may include the type of syringe 500 being fitted to the pump. The pump stores in an internal memory a database of known syringe types containing information such as syringe diameter and stroke. The infusion device firmware calculates the position of the syringe plunger and syringe piston based on movement of the syringe driver head and the type and size of the syringe. This allows the machine to display the calculation of volume infused, time elapsed, volume remaining and time remaining. As infusion continues and the driver head moves, these calculations can be updated, a flow rate can be determined based on at least in part the size of the syringe and the area and velocity of the piston, and the displayed information changed.

The disposable portion 302 of flow rate detector 300, 400 is seen mounted on a flange 507 near an exit port of the syringe 501. Once the disposable portion 302 is mounted, the reusable portion 504 may be connected lengthwise along the disposable portion 302, as shown in FIG. 5. Infusion device 500 may include one or more transducer ports 512 for connecting the electrical leads 336 of transducers 306, 308. In this manner the infusion device 500 (or monitoring system) may initiate transmission via one or more of the transducers 306, 308, or receive electrical signals representative of transducer measurements made by one or more of the transducers 306, 308. A microprocessor within infusion device 500 (or similarly situated monitoring system) may calculate flow rates as described with regard to FIG. 1A or 1B.

Figure 6:
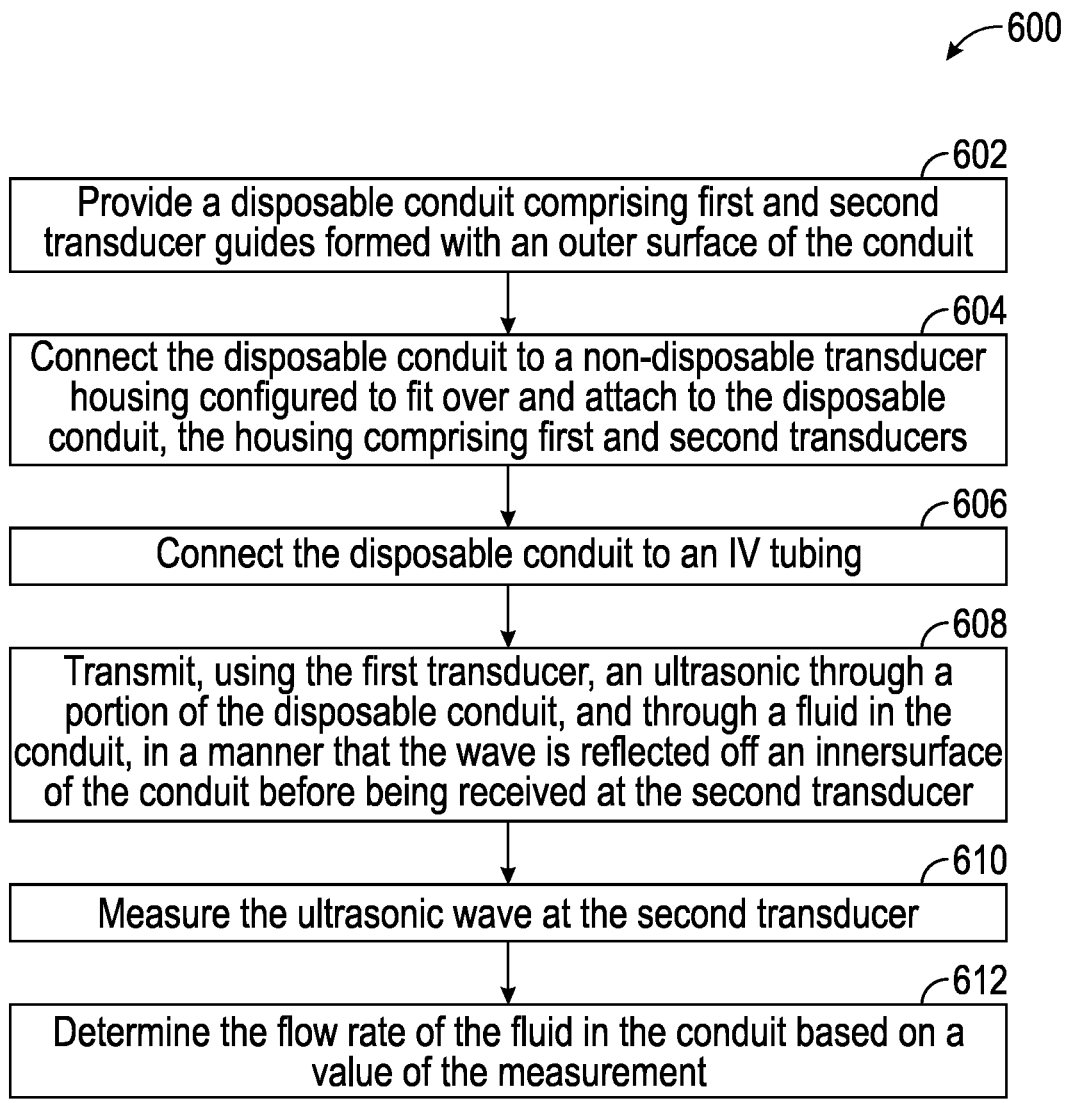
FIG. 6 depicts an example process for determining a flow rate of an IV line set, according to aspects of the subject technology.

FIG. 6 depicts an example process 600 for determining a flow rate of an IV line set, according to aspects of the subject technology. For explanatory purposes, the various blocks of example process 600 are described herein with reference to FIGS. 1 through 5, and the components and/or processes described herein. The one or more of the blocks of process 600 may be implemented, for example, by one or more computing devices including, for example, within infusion device 500. In some implementations, one or more of the blocks may be implemented based on one or more machine learning algorithms. In some implementations, one or more of the blocks may be implemented apart from other blocks, and by one or more different processors or devices. Further for explanatory purposes, the blocks of example process 600 are described as occurring in serial, or linearly. However, multiple blocks of example process 600 may occur in parallel. In addition, the blocks of example process 600 need not be performed in the order shown and/or one or more of the blocks of example process 600 need not be performed.

In the depicted example, a disposable conduit for sensing a flow rate is provided (602). The disposable conduit includes first and second transducer guides formed with an outer surface of the disposable conduit. Each transducer guide configured to position a respective transducer of a sensor chassis such that a transmission to or from each respective transducer occurs at an angle offset from a fluidic channel within the disposable conduit, and such that a transmission from one of the respective transducers passes through a first portion of the fluidic channel, through a fluid in the disposable conduit, reflects at least once off of an inner surface of the fluidic channel, and passes through a second portion of the fluidic channel to be received at the other respective transducer.

The disposable conduit is connected to a reusable transducer chassis configured to fit over and attach along a length of the disposable conduit (604). The reusable transducer chassis includes first and second transducers positioned such that, when the reusable transducer chassis is fitted over and attached to the disposable conduit, the first transducer is aligned with the first transducer guide of the disposable conduit and the second transducer is aligned with the second transducer guide to enable a transmission from the first transducer to pass through the first and second portions of the fluidic channel.

The disposable conduit is connected to an intravenous (IV) tubing (606).

Using the first transducer, an ultrasonic wave is transmitted through a portion of the disposable conduct corresponding to the first transducer guide, and through the fluid within the disposable conduit, in a manner that the ultrasonic wave is reflected off of an inner surface of the disposable conduit before being received at the second transducer, through the second transducer guide (608). According to various implementations, the ultrasonic wave is reflected at least once, and in some implementations, one or more times, off of the inner surface of the disposable conduit before being received at the second transducer, as shown in FIGS. 2A and 2B. The ultrasonic wave is then measured using the second transducer (610), and the flow rate of the fluid in the conduit is determined based on a value of the measurement (612).

The ultrasonic transmission may be transmitted according to the Z-method, V-method or W-method described with regard to FIG. 2A and FIG. 2B. Flow rates may be previously determined based on lab data and stored in a data-based, indexed by predetermined measured values. As described previously, for each of the V-method, W-method or Z-method, test flow rates may be implemented for each type of fluid (e.g., each type of medication) and, in some implementations, the size of tubing or conduit (which, e.g., may determine transit time), and respective values measured. The flow rates may then be indexed in a lookup table by the measured values and made available for use by an infusion device (e.g., device 500). For example, the table may be stored in a database (within a non-transitory memory) within the infusion device or made available to the infusion device by a server. Additionally or in the alternative, bias values that correct for a flow rate measured by the infusion device administering a medication (e.g., device 500) may be stored. In this regard, a bias value may be used by the infusion device to correct for a flow rate measured by the infusion device by some other mechanism. During operation, the flow rate or bias may be displayed on a display of the corresponding infusion device. In some implementations, the infusion device may display an indicator on the display screen, with the flow rate, indicating that the flow rate has been corrected (as a result of the ultrasonic measurement).

The determination of flow rates may be based on single measurements or a combination of measurements over a period of time (e.g., average or moving average). The determination of flow rate may be based on single results or a combination of flow rates over a period of time (e.g., average or moving average). In some implementations, the ranking may be assessed using a range of acceptable scores.

Once detected, the flow rate may be used to adjust or otherwise control the infusion device. For example, the system may include absolute limits for the flow rates and when the detected rate does not correspond to the limits, the infusion device may pause, alert, or take other action. The limits may be system-wide or dynamically determined based on the infusion being performed (e.g., volume, patient weight, patient age, drug type, etc.). A user interface may be provided to receive such configurations or thresholds.

Although the device and methods shown in FIGS. 1 through 6 discuss detecting flow rates, the described features may be used to detect or respond to air in line.

Many of the above-described devices, systems and methods, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 7:
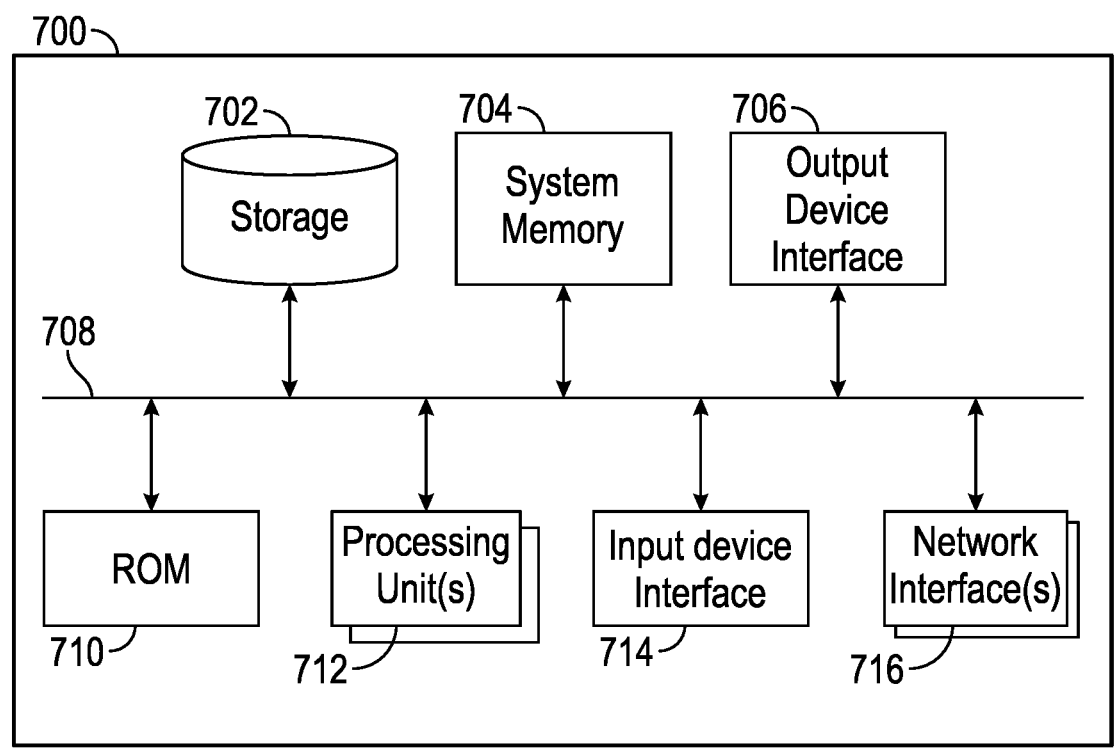
FIG. 7 is a conceptual diagram illustrating an example electronic system for determining a flow rate of an IV line set, according to aspects of the subject technology.

FIG. 7 is a conceptual diagram illustrating an example electronic system 700 for determining a flow rate of an IV line set, according to aspects of the subject technology. Electronic system 700 may be a computing device for execution of software associated with one or more components and processes provided by FIGS. 1 to 6, including but not limited to a controller, or computing hardware within pump 500. Electronic system 700 may be representative of a device used in connection or combination with the disclosure regarding FIGS. 1 to 6. In this regard, electronic system 700 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 700 may include various types of computer readable media and interfaces for various other types of computer readable media. In the depicted example, electronic system 700 includes a bus 708, processing unit(s) 712, a system memory 704, a read-only memory (ROM) 710, a permanent storage device 702, an input device interface 714, an output device interface 706, and one or more network interfaces 716. In some implementations, electronic system 600 may include or be integrated with other computing devices or circuitry for operation of the various components and processes previously described.

Bus 708 collectively represents all system, peripheral, and chipset buses that communicatively connect the numerous internal devices of electronic system 600. For instance, bus 708 communicatively connects processing unit(s) 712 with ROM 710, system memory 704, and permanent storage device 702.

From these various memory units, processing unit(s) 712 retrieves instructions to execute and data to process in order to execute the processes of the subject disclosure. The processing unit(s) can be a single processor or a multi-core processor in different implementations.

ROM 710 stores static data and instructions that are needed by processing unit(s) 712 and other modules of the electronic system. Permanent storage device 702, on the other hand, is a read-and-write memory device. This device is a non-volatile memory unit that stores instructions and data even when electronic system 700 is off. Some implementations of the subject disclosure use a mass-storage device (such as a magnetic or optical disk and its corresponding disk drive) as permanent storage device 702.

Other implementations use a removable storage device (such as a floppy disk, flash drive, and its corresponding disk drive) as permanent storage device 702. Like permanent storage device 702, system memory 704 is a read-and-write memory device. However, unlike storage device 702, system memory 704 is a volatile read-and-write memory, such a random access memory. System memory 704 stores some of the instructions and data that the processor needs at runtime. In some implementations, the processes of the subject disclosure are stored in system memory 704, permanent storage device 702, and/or ROM 710. From these various memory units, processing unit(s) 712 retrieves instructions to execute and data to process in order to execute the processes of some implementations.

Bus 708 also connects to input and output device interfaces 714 and 706. Input device interface 714 enables the user to communicate information and select commands to the electronic system. Input devices used with input device interface 714 include, e.g., alphanumeric keyboards and pointing devices (also called "cursor control devices"). Output device interfaces 706 enables, e.g., the display of images generated by the electronic system 600. Output devices used with output device interface 706 include, e.g., printers and display devices, such as cathode ray tubes (CRT) or liquid crystal displays (LCD). Some implementations include devices such as a touchscreen that functions as both input and output devices.

Also, as shown in FIG. 7, bus 708 also couples electronic system 700 to a network (not shown) through network interfaces 716. Network interfaces 716 may include, e.g., a wireless access point (e.g., Bluetooth or WiFi) or radio circuitry for connecting to a wireless access point. Network interfaces 716 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 600 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML, page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses:

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A flow rate detector comprising a reusable sensor chassis configured to fit over an outer surface of a disposable conduit section, the reusable sensor chassis configured to attach along a length of the of the disposable conduit section, and comprising first and second transducers configured to, when the reusable chassis is attached to a disposable conduit section, measure a flow rate of a fluid passing through the conduit section by measuring an electronic transmission between the first and second transducers through the fluid.

Clause 2. The flow rate detector of Clause 1, wherein the electronic transmission is reflected at least once off of an inner surface of the disposable conduit section between the first and second transducers.

Clause 3. The flow rate detector of Clause 2, wherein the electronic transmission is reflected three times off of the inner surface of the disposable conduit section before being received at a respective transducer.

Clause 4. The flow rate detector of any one of Clauses 1 through 3, wherein the reusable sensor chassis comprises one or more concaved portions that, when attached along the length of the disposable conduit section, conform to one or more raised portions of the disposable conduit section.

Clause 5. The flow rate detector of Clause 4, wherein the first and second transducers are positioned within the reusable sensor chassis such that, when the reusable sensor chassis is fitted over and attached to the disposable conduit section, the first transducer is aligned with a first transducer guide of the disposable conduit section and the second transducer is aligned with a second transducer guide of the disposable conduit section to enable a transmission from the first transducer to pass through first and second portions of the disposable conduit section.

Clause 6. The flow rate detector of any one of Clauses 1 through 5, wherein the reusable sensor chassis comprises an attachment guide at location corresponding to, when the reusable sensor chassis is fitted over and attached to the disposable conduit section, a corresponding attachment guide on the disposable conduit section, such that the reusable sensor chassis and the disposable conduit section are caused to connect together.

Clause 7. The flow rate detector of Clause 6, wherein a respective attachment guide comprises a magnet or other ferromagnetic material, and the disposable conduit section and the reusable sensor chassis are caused to connect together by a magnetic force and to align each of the first and second transducers with a corresponding transducer guide on the disposable conduit section.

Clause 8. A flow rate detection system comprising: a disposable conduit section comprising: (1) an input connector and an output connector configured to connect to an IV tubing, (2) a fluidic channel enabling fluid to flow between the input and output connectors, and (3) first and second transducer guides formed with an outer surface of the disposable conduit, each transducer guide configured to position a respective transducer for transmission to or from each respective transducer to occur at an angle offset from the fluidic channel, and such that a transmission from one of the respective transducers passes through a first portion of the fluidic channel, reflects at least once off of an inner surface of the fluidic channel, and passes through a second portion of the fluidic channel be received at the other respective transducer.

Clause 9. The flow rate detection system of Clause 8, further comprising: a reusable transducer chassis configured to fit over and attach along a length of the disposable conduit section, the reusable transducer chassis comprising first and second transducers positioned such that, when the reusable transducer chassis is fitted over and attached to the disposable conduit section, the first transducer is aligned with the first transducer guide of the disposable conduit section and the second transducer is aligned with the second transducer guide to enable a transmission from the first transducer to pass through the first and second portions of the fluidic channel.

Clause 10. The flow rate detection system of Clause 9, wherein the reusable transducer chassis comprises a first inverted cavity housing the first transducer and a second inverted cavity housing the second transducer, each inverted cavity configured to slide over a corresponding transducer guide and align a corresponding transducer with the corresponding transducer guide when the reusable transducer chassis is attached along the length of the disposable conduit.

Clause 11. The flow rate detection system of Clause 10, wherein at least a portion of each transducer guide is cylindrical with a flat surface configured to slide into a respective inverted cavity of the reusable transducer chassis and interface with a floor of the respective inverted cavity when the reusable transducer chassis is attached along the length of the disposable conduit.

Clause 12. The flow rate detection system of Clause 10, wherein the reusable transducer chassis and the disposable conduit section each comprise a magnet or other ferromagnetic material, respectively, at corresponding locations such that the reusable transducer chassis and the disposable conduit section are caused to connect together by a magnetic force and to align each of the first and second transducers with the corresponding transducer guide.

Clause 13. The flow rate detection system of any one of Clauses 9 through 12, wherein the input connector or the output connector is configured to connect to an end of a syringe.

Clause 14. The flow rate detection system of any one of Clauses 9 through 13, wherein the transmission from the first transducer passes through the first portion of the fluidic channel and is reflected three times off of the inner surface of the fluidic channel before being received at the second transducer Clause 15. The flow rate detection system of any one of Clauses 9 through 14, wherein the transmission comprises an ultrasonic wave.

Clause 16. The flow rate detection system of any one of Clauses 9 through 15, wherein a portion of the inner surface of the fluidic channel off of which the transmission reflects comprises an ultrasonic reflective material that is different than an ultrasonic transparent material forming other portions of the fluidic channel including the first portion of the fluidic channel through which the transmission from one of the respective transducers passes.

Clause 17. A method comprising: providing a disposable conduit for sensing a flow rate and comprising first and second transducer guides formed with an outer surface of the disposable conduit, each transducer guide configured to position a respective transducer of a sensor chassis such that a transmission to or from each respective transducer occurs at an angle offset from a fluidic channel within the disposable conduit, and such that a transmission from one of the respective transducers passes through a first portion of the fluidic channel, reflects at least once off of an inner surface of the fluidic channel, and passes through a second portion of the fluidic channel to be received at the other respective transducer.

Clause 18. The method of Clause 17, further comprising: connecting the disposable conduit to a reusable transducer chassis configured to fit over and attach along a length of the disposable conduit, the reusable transducer chassis comprising first and second transducers positioned such that, when the reusable transducer chassis is fitted over and attached to the disposable conduit, the first transducer is aligned with the first transducer guide of the disposable conduit and the second transducer is aligned with the second transducer guide to enable a transmission from the first transducer to pass through the first and second portions of the fluidic channel.

Clause 19. The method of Clause 18, further comprising: connecting the disposable conduit to an intravenous (IV) tubing; transmitting, using the first transducer, an ultrasonic wave through a portion of the disposable conduct corresponding to the first transducer guide, and through a fluid within the disposable conduit, in a manner that the ultrasonic wave is reflected off of an inner surface of the disposable conduit before being received at the second transducer, through the second transducer guide; and measuring the ultrasonic wave using the second transducer to obtain a measured value; and determining a flow rate of the fluid based on the measured value.

Clause 20. The method of Clause 19, wherein the ultrasonic wave is reflected two or more times off of the inner surface of the disposable conduit before being received at the second transducer.

Further Consideration:

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all implementations, or one or more implementations. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. A flow rate detector comprising:
a reusable sensor chassis configured to fit over an outer surface of a disposable conduit section, the reusable sensor chassis configured to attach along a length of the disposable conduit section by way of first and second transducer guides formed with an outer surface of the disposable conduit, and comprising first and second transducers configured to, when the reusable sensor chassis is attached to the disposable conduit section, measure a flow rate of a fluid passing through the disposable conduit section by measuring an electronic transmission between the first and second transducers through the fluid,
wherein the reusable sensor chassis comprises a first inverted cavity that houses the first transducer and a second inverted cavity that houses the second transducer, each inverted cavity configured to slide over a corresponding transducer guide and align a corresponding transducer with the corresponding transducer guide when the reusable sensor chassis is attached along the length of the disposable conduit,
wherein when each inverted cavity is slid over the respective transducer guide, a flat surface of the respective transducer guide slides into the respective inverted cavity of the inverted cavity and interfaces with a floor of the inverted cavity.

2. The flow rate detector of claim 1, wherein the electronic transmission is reflected at least once off of an inner surface of the disposable conduit section between the first and second transducers.

3. The flow rate detector of claim 2, wherein the electronic transmission is reflected three times off of the inner surface of the disposable conduit section before being received at a respective transducer.

4. The flow rate detector of claim 1, wherein the reusable sensor chassis comprises one or more concaved portions that, when attached along the length of the disposable conduit section, conform to one or more raised portions of the disposable conduit section.

5. The flow rate detector of claim 1, wherein the reusable sensor chassis comprises an attachment guide at location corresponding to, when the reusable sensor chassis is fitted over and attached to the disposable conduit section, a corresponding attachment guide on the disposable conduit section, such that the reusable sensor chassis and the disposable conduit section are caused to connect together.

6. The flow rate detector of claim 5, wherein a respective attachment guide comprises a magnet or other ferromagnetic material, and the disposable conduit section and the reusable sensor chassis are caused to connect together by a magnetic force and to align each of the first and second transducers with a corresponding transducer guide on the disposable conduit section.

7. A flow rate detection system comprising:
a disposable conduit section comprising:
(1) an input connector and an output connector configured to connect to an IV tubing,
(2) a fluidic channel enabling fluid to flow between the input and output connectors,
(3) first and second transducer guides formed with an outer surface of the disposable conduit section, each transducer guide configured to position a respective transducer for transmission to or from each respective transducer to occur at an angle offset from the fluidic channel, and such that a transmission from one of the respective transducers passes through a first portion of the fluidic channel, reflects at least once off of an inner surface of the fluidic channel, and passes through a second portion of the fluidic channel be received at the other respective transducer, and
a reusable transducer chassis configured to fit over and attach along a length of the disposable conduit section, the reusable transducer chassis comprising first and second transducers positioned such that, when the reusable transducer chassis is fitted over and attached to the disposable conduit section, the first transducer is aligned with the first transducer guide of the disposable conduit section and the second transducer is aligned with the second transducer guide to enable a transmission from the first transducer to pass through the first and second portions of the fluidic channel to be measured by the second transducer.

8. The flow rate detection system of claim 7, wherein the reusable transducer chassis comprises a first inverted cavity housing the first transducer and a second inverted cavity housing the second transducer, each inverted cavity configured to slide over a corresponding transducer guide and align a corresponding transducer with the corresponding transducer guide when the reusable transducer chassis is attached along the length of the disposable conduit section.

9. The flow rate detection system of claim 8, wherein at least a portion of the first and second inverted cavities and each transducer guide is cylindrical.

10. The flow rate detection system of claim 8, wherein the reusable transducer chassis and the disposable conduit section each comprise a magnet or other ferromagnetic material, respectively, at corresponding locations such that the reusable transducer chassis and the disposable conduit section are caused to connect together by a magnetic force and to align each of the first and second transducers with the corresponding transducer guide.

11. The flow rate detection system of claim 7, wherein the input connector or the output connector is configured to connect to an end of a syringe.

12. The flow rate detection system of claim 7, wherein the transmission from the first transducer passes through the first portion of the fluidic channel and is reflected three times off of the inner surface of the fluidic channel before being received at the second transducer.

13. The flow rate detection system of claim 7, wherein the transmission comprises an ultrasonic wave.

14. The flow rate detection system of claim 7, wherein a portion of the inner surface of the fluidic channel which the transmission reflects off of comprises an ultrasonic reflective material that is different than an ultrasonic transparent material forming other portions of the fluidic channel including the first portion of the fluidic channel through which the transmission from one of the respective transducers passes.

15. A method comprising:
providing a disposable conduit for sensing a flow rate and comprising first and second transducer guides formed with an outer surface of the disposable conduit; and
connecting the disposable conduit to a reusable transducer chassis configured to fit over and attach along a length of the disposable conduit,
wherein each transducer guide configured to, when the reusable transducer chassis is attached along the length of the disposable conduit, slide into a corresponding inverted cavity of the reusable transducer chassis such that a surface of the transducer guide interfaces with a floor of the corresponding inverted cavity and a respective transducer of the reusable transducer chassis is positioned such that a transmission to or from each respective transducer occurs at an angle offset from a fluidic channel within the disposable conduit, and such that the transmission from one of the respective transducers passes through a first portion of the fluidic channel, reflects at least once off of an inner surface of the fluidic channel, and passes through a second portion of the fluidic channel to be received at the other respective transducer.

16. The method of claim 15, further comprising:
the reusable transducer chassis comprising first and second transducers positioned such that, when the reusable transducer chassis is fitted over and attached to the disposable conduit, the first transducer is aligned with the first transducer guide of the disposable conduit and the second transducer is aligned with the second transducer guide to enable the transmission from the first transducer to pass through the first and second portions of the fluidic channel.

17. The method of claim 16, further comprising:
connecting the disposable conduit to an intravenous (IV) tubing;
transmitting, using the first transducer, an ultrasonic wave through a portion of the disposable conduit corresponding to the first transducer guide, and through a fluid within the disposable conduit, in a manner that the ultrasonic wave is reflected off of an inner surface of the disposable conduit before being received at the second transducer, through the second transducer guide; and
measuring the ultrasonic wave using the second transducer to obtain a measured value; and
determining a flow rate of the fluid based on the measured value.

18. The method of claim 17, wherein the ultrasonic wave is reflected two or more times off of the inner surface of the disposable conduit before being received at the second transducer.

* * * * *